US012636217B2

(12) United States Patent
Roh et al.

(10) Patent No.: US 12,636,217 B2
(45) Date of Patent: May 26, 2026

(54) DRIVING MODULE AND MOTION ASSISTANCE APPARATUS INCLUDING THE SAME

(71) Applicant: Samsung Electronics Co., Ltd., Suwon-si (KR)

(72) Inventors: Se-Gon Roh, Suwon-si (KR); Jeonghun Kim, Hwaseong-si (KR); Minhyung Lee, Anyang-si (KR); Youn Baek Lee, Yongin-si (KR); Jongwon Lee, Uiwang-si (KR); Byungjune Choi, Gunpo-si (KR); Hyun Do Choi, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 282 days.

(21) Appl. No.: 18/581,428

(22) Filed: Feb. 20, 2024

(65) Prior Publication Data

US 2024/0390210 A1 Nov. 28, 2024

Related U.S. Application Data

(60) Continuation of application No. 18/074,677, filed on Dec. 5, 2022, now Pat. No. 11,931,310, which is a
(Continued)

(30) Foreign Application Priority Data

Jan. 7, 2015 (KR) ........................ 10-2015-0002072

(51) Int. Cl.
*A61H 3/00* (2006.01)
*A61F 2/68* (2006.01)
(Continued)

(52) U.S. Cl.
CPC .................. *A61H 3/00* (2013.01); *A61F 2/68* (2013.01); *A61F 2/70* (2013.01); *A61H 1/0237* (2013.01);
(Continued)

(58) Field of Classification Search
CPC ........ A61H 3/00; A61H 1/02; A61H 2201/16; A61H 2201/14; A61H 2203/007;
(Continued)

(56) References Cited

U.S. PATENT DOCUMENTS 30,271 A * 10/1860 Vergnes ................ H01F 27/323
336/186
135,312 A * 1/1873 Bevelander ............ B65G 47/24
221/172
(Continued)

FOREIGN PATENT DOCUMENTS

JP 2006-075226 A 3/2006
JP 2006-320351 A 11/2006
(Continued)

OTHER PUBLICATIONS

U.S. Appl. No. 18/074,677, filed Dec. 5, 2022; Roh et al.
(Continued)

*Primary Examiner* — Garrett K Atkinson
(74) *Attorney, Agent, or Firm* — Nixon & Vanderhye P.C.

(57) ABSTRACT

A driving module including a driving source configured to generate power, a gear train including a decelerating gear set configured to receive driving power from the driving source and a ring gear attached to one side thereof, and a rotary joint including at least one planetary gear configured to rotate using power received from an output end of the decelerating gear set and to revolve along the ring gear is disclosed.

4 Claims, 13 Drawing Sheets

Related U.S. Application Data continuation of application No. 17/180,281, filed on Feb. 19, 2021, now Pat. No. 11,534,360, which is a continuation of application No. 16/410,247, filed on May 13, 2019, now Pat. No. 10,952,917, which is a division of application No. 16/263,531, filed on Jan. 31, 2019, now Pat. No. 10,952,915, which is a division of application No. 14/796,583, filed on Jul. 10, 2015, now Pat. No. 10,231,894.

(51) Int. Cl.

| | |
|---|---|
| *A61F 2/70* | (2006.01) |
| *A61H 1/02* | (2006.01) |
| *F16H 1/20* | (2006.01) |
| *F16H 1/28* | (2006.01) |
| *F16H 37/04* | (2006.01) |
| *F16H 57/02* | (2012.01) |

(52) U.S. Cl.
CPC ......... *A61H 1/0244* (2013.01); *A61H 1/0274* (2013.01); *F16H 1/20* (2013.01); *F16H 57/02* (2013.01); *A61H 2003/007* (2013.01); *A61H 2201/1215* (2013.01); *A61H 2201/1472* (2013.01); *A61H 2201/1628* (2013.01); *A61H 2201/164* (2013.01); *A61H 2201/165* (2013.01); *A61H 2201/1676* (2013.01); *A61H 2201/5007* (2013.01); *F16H 1/28* (2013.01); *F16H 37/041* (2013.01)

(58) Field of Classification Search
CPC ............ A61H 2201/50; A61H 2201/12; A61H 1/0237; A61H 1/0244; A61H 1/0274; A61H 2201/1472; A61H 2201/1628; A61H 2201/164; A61H 2201/1676; A61H 2201/1215; A61H 2201/165; A61H 2201/5007; A61H 2201/0157; A61H 2003/007; A61H 1/0262; A61H 3/008; A61H 2201/1223; A61H 2201/1463; A61H 2205/10; A61H 1/0247; F16H 57/02; F16H 1/28; F16H 1/20; F16H 37/041; A61F 2/68; A61F 1/28; A61F 1/02; A61F 37/04; A61F 2/70
See application file for complete search history.

(56) References Cited

U.S. PATENT DOCUMENTS

| | | | | |
|---|---|---|---|---|
| 174,690 | A | * | 3/1876 | Macy ..................... G02B 27/08 |
| | | | | 359/617 |
| 198,116 | A | * | 12/1877 | Johnson ................... A01C 7/18 |
| | | | | 111/43 |
| 222,532 | A | * | 12/1879 | Raedler et al. ......... C04B 28/02 |
| | | | | 264/333 |
| 298,939 | A | * | 5/1884 | Briggs ...................... C05F 3/00 |
| | | | | 71/25 |
| 4,715,243 | A | * | 12/1987 | Morishita ............... F16H 55/06 |
| | | | | 74/DIG. 10 |
| 5,067,479 | A | * | 11/1991 | Saringer .............. A61H 1/0285 |
| | | | | 601/40 |
| 5,161,036 | A | * | 11/1992 | Mannichi ............. H04N 1/4051 |
| | | | | 358/448 |
| 5,683,351 | A | * | 11/1997 | Kaiser .................. A61H 1/0288 |
| | | | | 601/40 |
| 6,198,182 | B1 | | 3/2001 | Bustamante et al. |
| 7,377,875 | B2 | * | 5/2008 | Shiina .................. F16H 35/008 |
| | | | | 475/331 |
| 7,404,782 | B2 | * | 7/2008 | Kudoh ................... A61H 3/008 |
| | | | | 475/903 |

| | | | | |
|---|---|---|---|---|
| 7,559,909 | B2 | * | 7/2009 | Katoh .................. A61H 1/0255 |
| | | | | 602/26 |
| 7,998,096 | B1 | * | 8/2011 | Skoog ...................... A61H 3/00 |
| | | | | 601/5 |
| 8,588,651 | B2 | * | 11/2013 | Matsuda .................. F16H 1/46 |
| | | | | 399/167 |
| 8,671,788 | B2 | * | 3/2014 | Lim ...................... F16H 57/043 |
| | | | | 74/89.11 |
| 9,351,900 | B2 | * | 5/2016 | Walsh ................ A63B 23/0355 |
| 9,581,220 | B2 | * | 2/2017 | Kim ...................... H02K 7/116 |
| 10,231,894 | B2 | | 3/2019 | Roh et al. |
| 10,952,915 | B2 | | 3/2021 | Roh et al. |
| 10,952,917 | B2 | | 3/2021 | Roh et al. |
| 11,534,360 | B2 | | 12/2022 | Roh et al. |
| 2002/0077708 | A1 | * | 6/2002 | Iversen .................. A61F 2/585 |
| | | | | 623/64 |
| 2003/0222532 | A1 | * | 12/2003 | Hsu ...................... F16H 57/033 |
| | | | | 310/68 R |
| 2005/0075953 | A1 | * | 4/2005 | Lee ......................... G06Q 40/04 |
| | | | | 705/28 |
| 2006/0135312 | A1 | * | 6/2006 | Shiina .................. F16H 35/008 |
| | | | | 475/339 |
| 2007/0106190 | A1 | | 5/2007 | Katoh et al. |
| 2008/0161937 | A1 | | 7/2008 | Sankai |
| 2009/0299480 | A1 | * | 12/2009 | Gilbert .................. A61F 5/0125 |
| | | | | 623/18.11 |
| 2010/0198116 | A1 | * | 8/2010 | Hirata .................. A61H 1/0244 |
| | | | | 601/34 |
| 2011/0066093 | A1 | * | 3/2011 | Vess ...................... A61H 11/00 |
| | | | | 601/151 |
| 2011/0293328 | A1 | * | 12/2011 | Matsuda ............ G03G 21/1647 |
| | | | | 399/167 |
| 2012/0174690 | A1 | * | 7/2012 | Lim ...................... F16H 19/04 |
| | | | | 74/29 |
| 2014/0298939 | A1 | * | 10/2014 | Kim ...................... B25J 9/126 |
| | | | | 74/411.5 |
| 2015/0196450 | A1 | * | 7/2015 | Lee ...................... A61H 1/0266 |
| | | | | 901/28 |
| 2015/0321341 | A1 | * | 11/2015 | Smith ...................... A61H 3/00 |
| | | | | 623/57 |
| 2016/0015589 | A1 | * | 1/2016 | Lee ...................... A61H 1/024 |
| | | | | 602/16 |
| 2016/0030271 | A1 | * | 2/2016 | Roh ...................... A61H 1/0244 |
| | | | | 74/89.22 |
| 2016/0193102 | A1 | * | 7/2016 | Roh ........................ F16H 57/02 |
| | | | | 475/343 |
| 2016/0317375 | A1 | * | 11/2016 | Simon ..................... A61F 2/605 |

FOREIGN PATENT DOCUMENTS

| | | | |
|---|---|---|---|
| JP | 2009-095645 | A | 5/2009 |
| JP | 2010-000204 | A | 1/2010 |
| JP | 2011-131025 | A | 7/2011 |
| JP | 2012-165822 | A | 9/2012 |
| JP | 2013-000296 | A | 1/2013 |
| JP | 5161036 | B2 | 3/2013 |
| JP | 2013-233406 | | 11/2013 |
| KR | 2005-0075953 | A | 7/2005 |
| KR | 10-2012-0124677 | | 11/2012 |
| KR | 10-1417895 | B1 | 7/2014 |

OTHER PUBLICATIONS

U.S. Appl. No. 17/180,281, filed Feb. 19, 2021; Roh et al.
U.S. Appl. No. 16/410,247, filed May 13, 2019; Roh et al.
U.S. Appl. No. 16/263,531, filed Jan. 31, 2019; Roh et al.
U.S. Appl. No. 14/796,583, filed Jul. 10, 2015; Roh et al.
Notice of Allowance issued Sep. 28, 2021, in Korean Application No. 10-2015-0002072.
Non-Final Office Action issued Nov. 30, 2017, in corresponding U.S. Appl. No. 14/796,583.
Final Office Action issued Apr. 5, 2018, in corresponding U.S. Appl. No. 14/796,583.
Notice of Allowance issued on Nov. 1, 2018, in corresponding U.S. Appl. No. 14/796,583.

(56)　　　　　　　References Cited

OTHER PUBLICATIONS

Non-Final Office Action issued Apr. 6, 2020, in corresponding U.S. Appl. No. 16/263,531.

Notice of Allowance issued on Jul. 27, 2020, in corresponding U.S. Appl. No. 16/263,531.

Final Office Action issued Aug. 6, 2020, in corresponding U.S. Appl. No. 16/410,247.

Notice of Allowance issued on Nov. 18, 2020, in corresponding U.S. Appl. No. 16/410,247.

Notice of Allowance issued on Nov. 20, 2020, in corresponding U.S. Appl. No. 16/263,531.

* cited by examiner

<u>100</u>

100

100

<u>100</u>

DRIVING MODULE AND MOTION ASSISTANCE APPARATUS INCLUDING THE SAME

CROSS-REFERENCE TO RELATED APPLICATION

This application is a Continuation of U.S. application Ser. No. 18/074,677, filed Dec. 5, 2022, which is a Continuation of U.S. application Ser. No. 17/180,281, filed Feb. 19, 2021 (U.S. Pat. No. 11,534,360), which is a Continuation of U.S. application Ser. No. 16/410,247, filed May 13, 2019 (now U.S. Pat. No. 10,952,917), which is a Divisional of U.S. application Ser. No. 16/263,531, filed Jan. 31, 2019 (now U.S. Pat. No. 10,952,915), which is a Divisional of U.S. application Ser. No. 14/796,583, filed Jul. 10, 2015 (now U.S. Pat. No. 10,231,894), all which claim priority to KR 10-2015-0002072, filed Jan. 7, 2015, the entire contents of which are all hereby incorporated herein by reference in their entireties.

BACKGROUND

1. Field

Example embodiments relate to a driving module and/or a motion assistance apparatus including the same.

2. Description of the Related Art

Biped walking may aid a human in performing various daily activities by freeing the hands of the human during walking. When experiencing difficulties in such significant walking, a human body may be exposed to a number of issues. For example, a decrease in muscular strength may restrict physical activities and cause a reduction in muscle mass, energy consumption, and metabolism.

Walking assistance robots/walking assistance devices are being developed to aid those people having difficulties in walking to be able to walk with less difficulty. Such robots/devices may be worn on/attached to a lower body of a user to intensify muscular strength and alleviate a burden by weight during walking or standing on a level ground, a slope, or stairs.

In general, the robots/devices may have a structure to assist motions of joints of a lower body, for example, hip joints, knee joints, and ankle joints using an actuator. In the past, such robots/devices were developed to assist walking/intensify muscular strength of a patient. However, recently, the robots/devices are being developed to improve walking abilities for military purposes, manufacturing purposes, and general walking assistance purposes.

For example, to transmit a force and a torque generated by the actuator to joints of a user, a wearable portion acting as an interface between joints of the user and the device may be provided to be attached to or to enclose a body of the user. When driving power is transmitted in a direction in which a joint portion of the device connected to the wearable portion matches a moving direction of the joint of the user, the force and the torque may be applied appropriately without causing inconvenience. A driving source may include a motor and a decelerator, and may be disposed at a position corresponding to an axis of rotation of the joint of the user. The wearable portion may be provided in a form of a belt or a band so that a frame connected to the driving source may be attached to a leg portion of the user. Such a structure may be an external skeleton structure in which the driving source and the wearable portion are relatively thick, and may be worn over clothing to be exposed to an outside.

SUMMARY

Some example embodiments relate to a driving module.

In some example embodiments, the driving module may include a driving source configured to generate power, a gear train including a decelerating gear set configured to rotate using power received from the driving source, a joint aligning ring rotatably inserted into one side of the gear train, a rotary joint attached to the joint aligning ring, and configured to rotate using power received from the gear train, and a joint bearing disposed between the joint aligning ring and the rotary joint, and attached to the gear train.

The gear train may further include a first frame and a second frame configured to cover the decelerating gear set, and axes of rotation of gears included in the decelerating gear set may be formed as an integral body on at least one of the first frame and the second frame.

The decelerating gear set may include a base gear configured to act as an output end of the decelerating gear set, and at least one spur gear engaged between the driving source and the base gear.

One of the first frame and the second frame may include a cover portion configured to cover the at least one spur gear, and an edge portion connected to the cover portion, and on an outside of which the joint aligning ring is disposed.

The gear train may further include a ring gear attached to an inner side of the edge portion. The rotary joint may include at least one planetary gear engaged with the ring gear, and an axis of rotation of the planetary gear, and the axis of rotation of the planetary gear may be formed as an integral body on the rotary joint.

The base gear may include two gears having different diameters, and a small-diameter gear between the two gears of the base gear may be engaged with the planetary gear.

The planetary gear may include two gears having different diameters, and a large-diameter gear between the two gears of the planetary gear may be engaged with the small-diameter gear between the two gears of the base gear.

The gear train may further include a receiving protrusion including a groove configured to receive an axis of rotation of the rotary joint, a first bearing disposed between an inner wall of the groove and the axis of rotation of the rotary joint, and a second bearing disposed between an outer side of the receiving protrusion and an inner side of the base gear.

The rotary joint may include a rotation axis groove formed along a circumference of an axis of rotation of the rotary joint, and a third bearing disposed between a cylindrical end portion protruding from the base gear and an inner wall of the rotation axis groove.

The decelerating gear set may include an input gear connected to a shaft of the driving source, an idle gear engaged with the input gear, and a base gear engaged with the idle gear. Diameters of the input gear, the idle gear, and the base gear may increase sequentially in an order of power transmission.

The joint bearing may be configured to support at least one of an inner side of a contour of the joint aligning ring and an inner side of a contour of the rotary joint.

Other example embodiments relate to a driving module.

In some example embodiments, the driving module may include a driving source configured to generate power, a gear train including a decelerating gear set configured to receive driving power from the driving source, and a ring gear attached to one side thereof, and a rotary joint including at least one planetary gear configured to rotate using power received from an output end of the decelerating gear set, and to revolve along the ring gear.

An axis of rotation of the at least one planetary gear may be formed as an integral body on the rotary joint.

The decelerating gear set may include a base gear configured to act as the output end. The base gear may include two gears having different diameters, and a small-diameter gear between the two gears may be engaged with the planetary gear.

The gear train may include a joint aligning ring fastened to the rotary joint, and the driving module may further include a joint bearing attached to one side of the gear train, and configured to prevent a separation of the joint aligning ring from the gear train.

The joint bearing may be a thin section bearing configured to reduce a torsion of the rotary joint.

Other example embodiments relate to a motion assistance apparatus.

In some example embodiments, the motion assistance apparatus may include a fixing module configured to be attached to a user, a driving module including a driving source disposed on one side of the fixing module, a gear train configured to receive driving power from the driving source, and a rotary joint including at least one planetary gear connected to an output end of the gear train, and a supporting module configured to support a portion of a body of the user, and to be driven by the driving module.

An axis of rotation of the at least one planetary gear may be formed as an integral body on an inner side of the rotary joint.

The driving source may be attached to the gear train, and the rotary joint may be configured to relatively rotate with respect to the gear train using the driving power.

The driving source may be detachable from the gear train, and the gear train may be detachable from the rotary joint.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
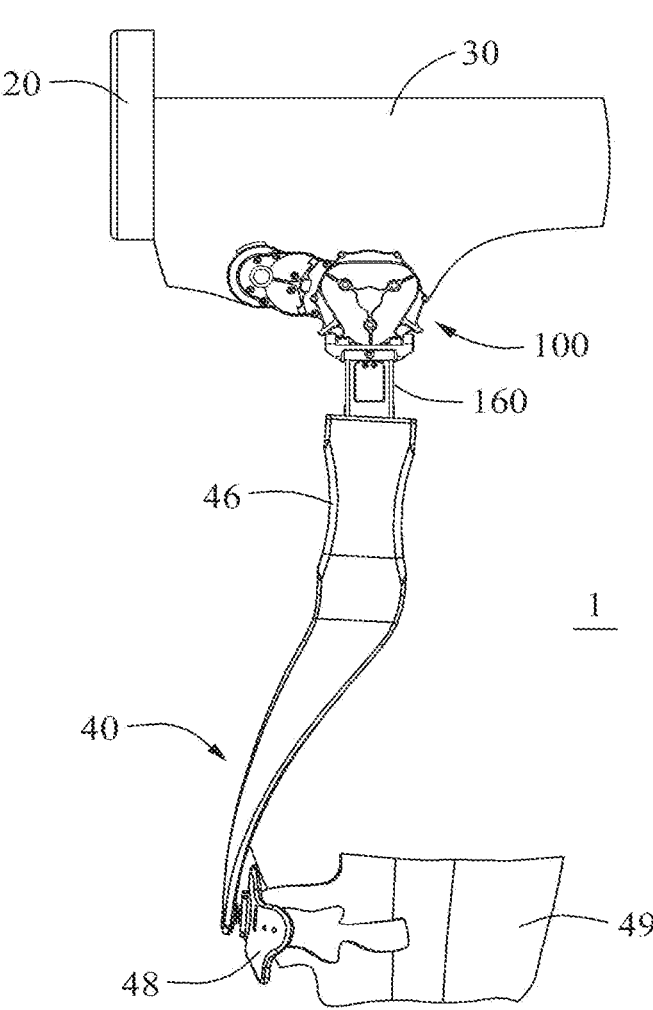
FIG. 1 is a side view of a motion assistance apparatus according to example embodiments.

Hereinafter, some example embodiments will be described in detail with reference to the accompanying drawings. Regarding the reference numerals assigned to the elements in the drawings, it should be noted that like elements will be designated by like reference numerals, wherever possible, even though they are shown in different drawings. Also, in the description of the example embodiments, detailed description of well-known related structures or functions will be omitted.

It should be understood, however, that there is no intent to limit this disclosure to the particular example embodiments disclosed. On the contrary, the example embodiments are to cover all modifications, equivalents, and alternatives falling within the scope of example embodiments.

In addition, terms such as first, second, A, B, (a), (b), and the like may be used herein to describe components. Each of these terminologies is not used to define an essence, order or sequence of a corresponding component but is used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 2:
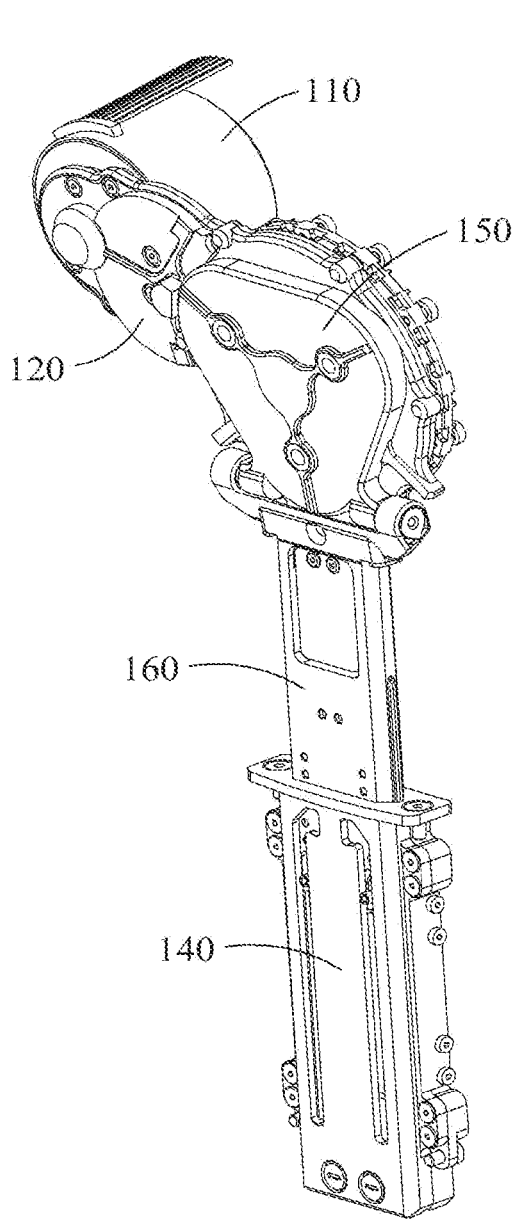
FIG. 2 is a perspective view of a driving module according to example embodiments.

FIG. 1 is a side view of a motion assistance apparatus 1 according to example embodiments, and FIG. 2 is a perspective view of a driving module 100 according to example embodiments.

Referring to FIG. 1, the motion assistance apparatus 1 may be worn by a user to assist a motion of the user.

The user may be, for example, a human, an animal, or a robot. However, example embodiments are not limited thereto. Although FIG. 1 illustrates a case in which the motion assistance apparatus 1 assists a motion of a thigh of the user, the motion assistance apparatus 1 may assist a motion of another part of an upper body, for example, a hand, an upper arm, and a lower arm of the user, or a motion of another part of a lower body, for example, a foot, and a calf of the user. Thus, the motion assistance apparatus 1 may assist a motion of a part of the user.

The motion assistance apparatus 1 may include a fixing module 30, a supporting module 40, the driving module 100, and a controller 20 configured to control the driving module 100.

The driving module 100 may include a driving source 110 disposed on one side of the fixing module 30, a gear train 120 configured to receive driving power from the driving source 110, and a rotary joint 150 including at least one planetary gear connected to an output end of the gear train 120. A connecting member 160 may be connected to the rotary joint 150. An insertion member 140 to be inserted into a supporting frame 46 may be connected to the connecting member 160.

The driving module 100 may be disposed on a hip joint to drive a joint portion of the motion assistance apparatus 1. Two driving modules 100 may be disposed on left and right hip joints to assist rotary motions of the left and right hip joints, respectively.

The driving module 100 will be described in detail later.

The fixing module 30 may be attached to the user. The fixing module 30 may be in contact with at least a portion of an outer surface of the user, and may be provided to cover the outer surface of the user. The fixing module 30 may include a curved surface to be in contact with the user. For example, the fixing module 30 may be attached to one or more sides of a waist of the user.

The supporting module 40 may include the supporting frame 46. The supporting frame 46 coupled to the connecting member 160 may rotate in a direction in which the connecting member 160 is rotated by the driving module 100. The supporting module 40 may further include a pressurizing member 48 connected from the supporting frame 46, and a supporting member 49.

The pressurizing member 48 may be connected to one or more sides of the supporting frame 46. For example, the pressurizing member 48 may be disposed on one side of a leg of the user to pull or push a thigh of the user. The pressurizing member 48 may be disposed on a front surface of the thigh of the user.

The supporting member 49 may be connected to one side of the pressurizing member 48. For example, the supporting member 49 may be disposed to cover a circumference of at least a portion of the thigh of the user, thereby preventing a separation of the thigh of the user from the supporting frame 44. The supporting member 49 may be disposed on an opposite side of the pressurizing member 48 from the thigh of the user.

A torque generated by the driving module 100 may be transmitted to the supporting module 40 through the connecting member 160. The torque transmitted through the supporting module 40 may be used to lift the thigh of the user through the pressurizing member 48, thereby assisting a motion of the user.

The controller 20 may include a processor and a memory (not shown).

The memory may be any device capable of storing data including magnetic storage, flash storage, etc. The processor may be any device capable of processing data including, for example, a microprocessor configured to carry out specific operations by performing arithmetical, logical, and input/output operations based on input data, or capable of executing instructions included in computer readable code stored in the memory. The processor may be a logic chip, for example, a central processing unit (CPU), a controller, or an application-specific integrated circuit (ASIC), that when, executing the instructions stored in the memory, configures the processor as a special purpose machine to control the driving module 100.

Figure 3:
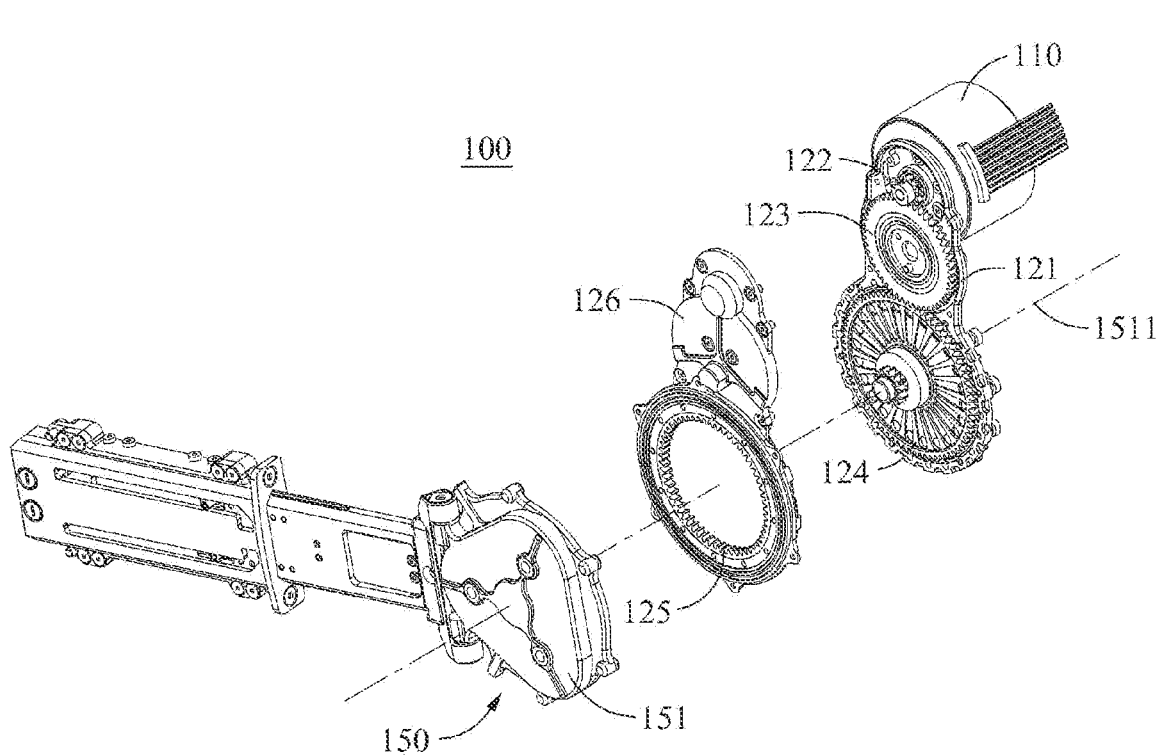
FIG. 3 is an exploded perspective view of a driving module according to example embodiments.
Figure 4:
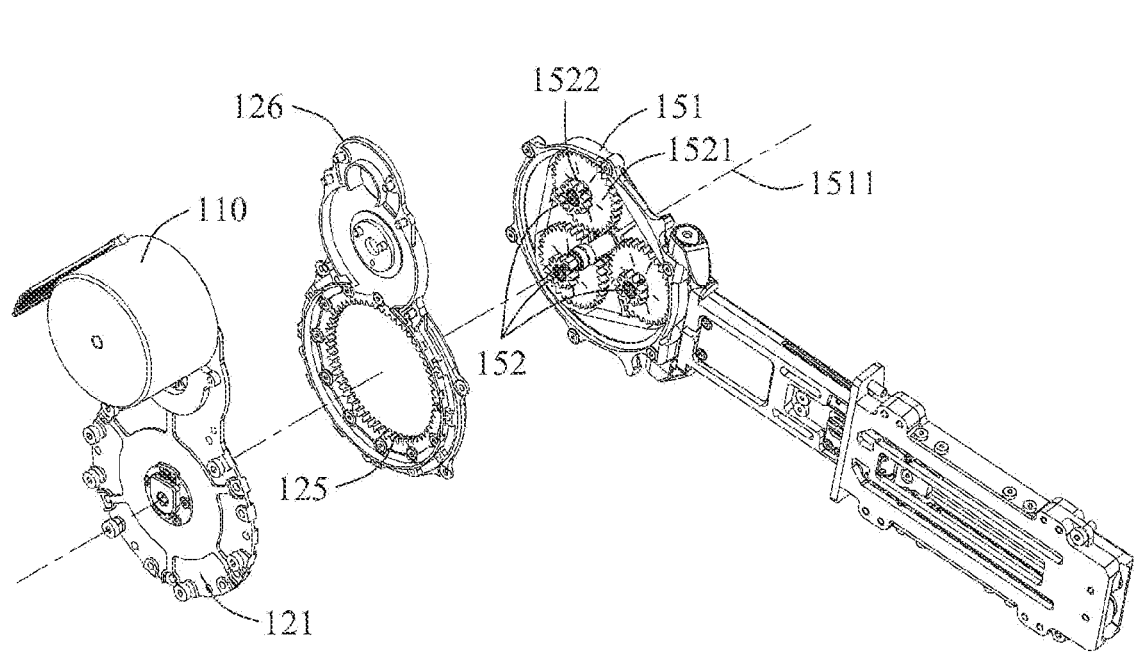
FIG. 4 is an exploded perspective view of the driving module of FIG. 3, viewed from another angle.

FIG. 3 is an exploded perspective view of the driving module 100 according to example embodiments, and FIG. 4 is an exploded perspective view of the driving module 100 of FIG. 3, viewed from another angle. In detail, FIG. 3 illustrates the driving module 100 viewed from the rotary joint 150, and FIG. 4 illustrates the driving module 100 viewed from the driving source 110.

Figure 5:
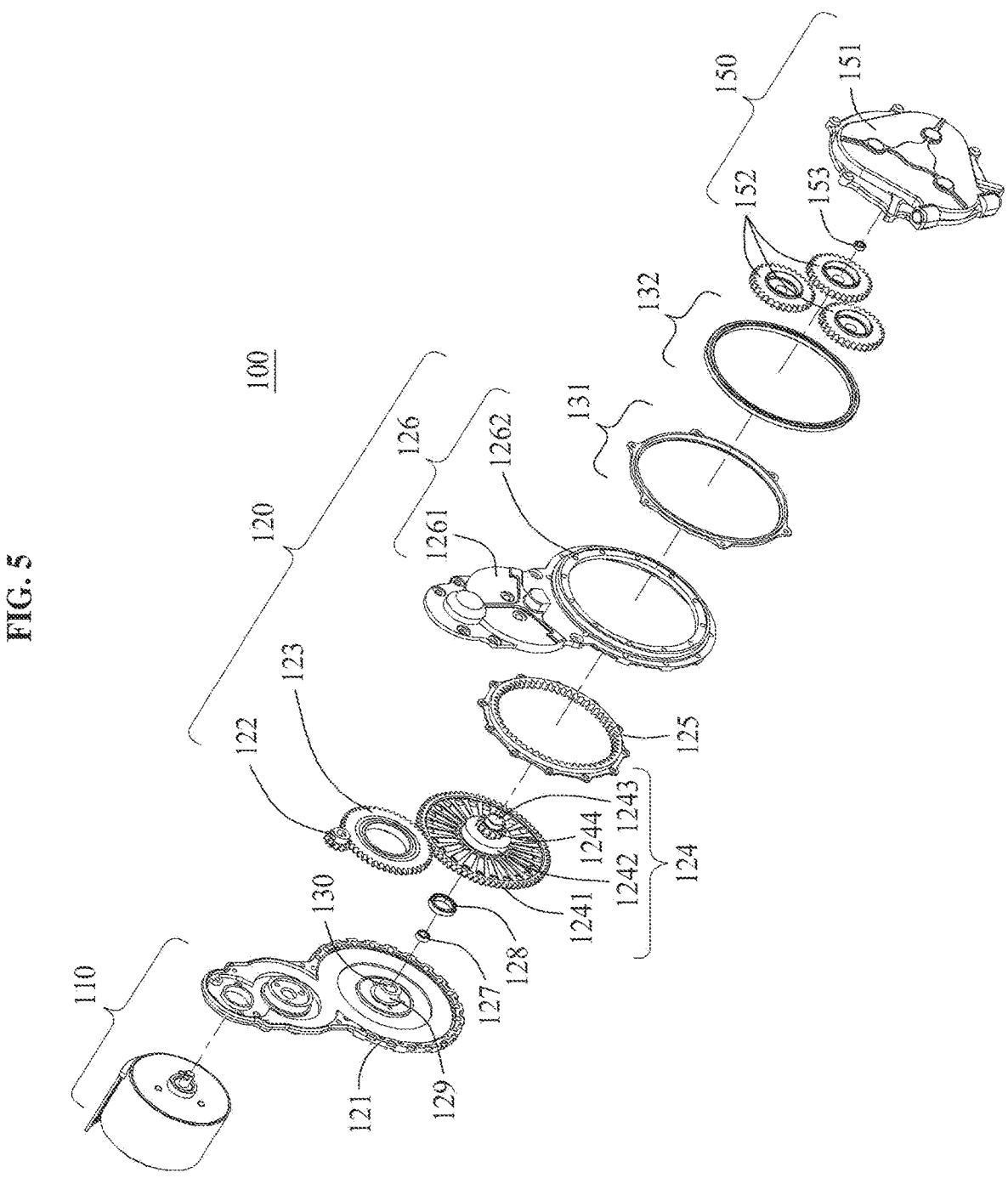
FIG. 5 is an exploded perspective view of a driving module according to example embodiments.
Figure 6:
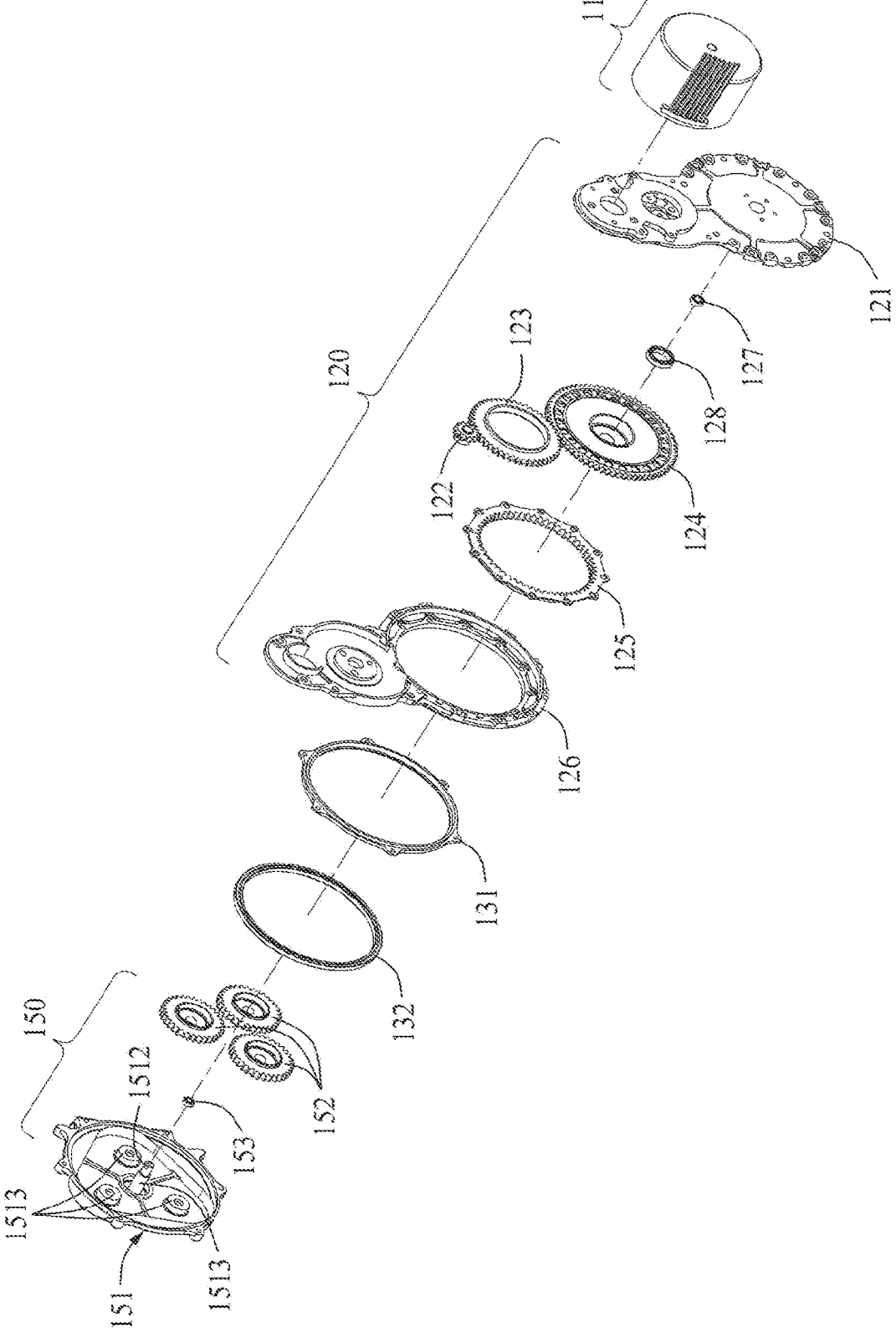
FIG. 6 is an exploded perspective view of the driving module of FIG. 5, viewed from another angle.

FIG. 5 is an exploded perspective view of the driving module 100 according to example embodiments, and FIG. 6 is an exploded perspective view of the driving module 100 of FIG. 5, viewed from another angle. In detail, FIG. 5 illustrates the driving module 100 viewed from the rotary joint 150, and FIG. 6 illustrates the driving module 100 viewed from the driving source 110.

Referring to FIGS. 3 to 6, the driving module 100 may include the driving source 110 configured to generate power, the gear train 120 configured to receive driving power from the driving source 110, a joint aligning ring 131 rotatably inserted into one side of the gear train 120, the rotary joint 150 attached to the joint aligning ring 131 and configured to rotate using power received from the gear train 120, and a joint bearing 132 disposed between the joint aligning ring 131 and the rotary joint 150 and attached to the gear train 120.

The driving source 110 may generate power to be used to drive the rotary joint 150. The driving source 110 may be disposed, for example, in a space between a thigh and a hip of the user. The driving source 110 may be, for example, an electric motor. However, the type of the driving source 110 is not limited thereto.

The gear train 120 may be driven using power received from the driving source 110. The gear train 120 may include a decelerating gear set including gears 122, 123, and 124, a ring gear 125 attached to one side thereof, and a first frame 121 and a second frame 126 configured to cover the decelerating gear set.

The decelerating gear set may decrease a rotation velocity of a rotary motion transmitted from the driving module 100 and generate a relatively great torque. The decelerating gear set may include, for example, spur gears or helical gears. A gear acting as an output end of the decelerating gear set may be referred to as the base gear 124. The base gear 124 may include two gears having different diameters. A small-diameter gear between the two gears of the base gear 125 may act as a sun gear to be engaged with a planetary gear 152.

Axes of rotation of the plurality of gears 122, 123, and 124 in the decelerating gear set may be formed as an integral body on the first frame 121. By providing the axes of rotation of the gears 122, 123, and 124 constituting the decelerating gear set as an integral body on the first frame 121, additional components and spaces to be used to fix the axes of rotation of the gears 122, 123, and 124 to the first frame 121 may be unnecessary. Thus, a size of the gear train 120 may be minimized.

The first frame 121 may be provided in a shape of a thin plate in which a small-sized circle, a medium-sized circle overlapping a portion of the small-sized circle, and a large-sized circle overlapping a portion of the medium-sized circle are arranged sequentially, based on a shape of the decelerating gear set.

The driving source 110 may be connected to one surface of the first frame 121, and the second frame 126 having substantially the same contour as the first frame 121 may be connected to an opposite surface of the first frame 121. Bolt holes may be provided along the contours of the first frame 121 and the second frame 126 to couple the first frame 121 and the second frame 126.

The second frame 126 may include a cover portion 1261 configured to cover at least one gear in the decelerating gear set, and an edge portion 1262 connected to the cover portion 1261 and on an outside of which the joint aligning ring 131 is disposed. The cover portion 1261 and the edge portion 1262 may be formed as an integrated single frame.

The ring gear 125 may be attached to an inner side of the edge portion 1262. The edge portion 1262 may be disposed along a circumference of a hollow having a size that may expose teeth of the ring gear 125 protruding toward a center of the circumference. The planetary gear 152 may penetrate through the hollow and be engaged with the ring gear 125.

The joint bearing 132 may be disposed on an outer side of the edge portion 1262. The joint bearing 132 may have a large diameter sufficient to firmly support a rotary cover 151 of the rotary joint 150. The joint bearing 132 may be attached to the second frame 126 to prevent a separation of the joint aligning ring 131. The joint bearing 132 may support at least one of an inner side of a contour of the joint aligning ring 131 and an inner side of a contour of the rotary joint 150. A thin section bearing may be used as the joint bearing 132.

The joint aligning ring 131 to be attached to the rotary joint 150 may be disposed between the second frame 126 and the joint bearing 132. The joint aligning ring 131 may rotate between the second frame 126 and the joint bearing 132. The joint aligning ring 131 may be inserted into a portion protruding from the second frame 126 toward the rotary joint 150. For example, a portion protruding toward a circumference of the joint aligning ring 131 and a portion protruding toward an outer side of the rotary cover 151 may be coupled using an adhesive or bolts.

The rotary joint 150 may rotate using power received from the output end of the gear train 120. The rotary joint 150 may be rotatably connected to the gear train 120 using the joint aligning ring 131. A shape of the contour of the rotary joint 150 may have a size corresponding to the large-sized circle of the first frame 121. The rotary joint 150 may be modularized to be detachable from the gear train 120. The rotary joint 150 may include the rotary cover 151 configured to cover the hollow of the edge portion 1262, the at least one planetary gear 152, and a third bearing 153.

The rotary cover 151 may be a shaft-integrated frame in which an axis of rotation of the at least one planetary gear 152 is configured as an integral body. The rotary cover 151 may include a joint connection link configured to rotatably connect the connecting member 160 to the rotary joint 150.

The axis of rotation of the at least one planetary gear 152 may be formed as an integral body with the rotary cover 151, similar to the first frame 121 of the gear train 120.

Hereinafter, descriptions will be provided based on an order of power transmission.

A torque generated by the driving source 110 of the gear train 120 may be transmitted to the input gear 122, also referred to as a driving gear, of the decelerating gear set, and transmitted to the planetary gear 152 through the idle gear 123 and the base gear 124.

The input gear 122 may be connected directly to an axis of rotation of the driving source 110, or connected to the axis of rotation of the driving source 110 through coupling. The idle gear 123 may be engaged with the input gear 122, and the base gear 124 may be engaged with the idle gear 123. Diameters of the input gear 122, the idle gear 123, and the base gear 124 may increase sequentially in the order of power transmission. The base gear 124 may act as an output end of the decelerating gear set.

The base gear 124 may include two gears 1241 and 1244 having different diameters, including a large-diameter gear 1241 and a small-diameter gear 1244. The small-diameter gear 1244 of the base gear 124 may be engaged with the planetary gear 152. The small-diameter gear 1244 may also be referred to as a sun gear. The large-diameter gear 1241 of the base gear 124 may be engaged with the idle gear 123.

A Cylinder 1242 is located between the large-diameter gear 1241 and a small-diameter gear 1244. The small-diameter gear 1244 is moved from the large-diameter gear 1241 to the central axis of the base gear 124 to broaden the gap between them. The height of The Cylinder 1242 is selected up to the point which the small-diameter gear 1244 and the planetary gear 152 are engaged. A diameter of The Cylinder 1242 is smaller than the diameter of large-diameter gear 1241 and larger than the diameter of a small-diameter gear 1244.

The base gear 124 may be a compound gear. The base gear 124 may be an integrated gear sharing a common axis with the small-diameter gear 1244 protruding from the large-diameter gear 1241. The small-diameter gear 1244 may act as a sun gear in a relationship with the planetary gear 152.

A final torque generated by the driving source 110 and to be transmitted to an output end may be transmitted to the small-diameter gear 1244 protruding from the base gear 124.

The torque transmitted to the small-diameter gear 1244 may be transmitted to three planetary gears 152. When the planetary gears 152 rotate along an inner circumference of the ring gear 125 attached to the second frame 126, the planetary gears 152 may simultaneously rotate while being engaged with the ring gear 125 and revolve on an axis of rotation 1511 of the rotary joint 150.

Axes of rotation of the planetary gears 152 may be fixed, and the rotary cover 151 of the rotary joint 150 may rotate on the axis of rotation 1511 of the rotary joint 150. Thus, the entire rotary joint 150 may rotate in a forward or backward direction.

The gear train 120 may include a receiving protrusion 129 including a groove 130 configured to receive the axis of rotation 1511 of the rotary joint 150, a first bearing 127 disposed between an inner wall of the groove 130 and the axis of rotation 1511 of the rotary joint 150, and a second bearing 128 disposed between an outer side of the receiving protrusion 129 and an inner side of the base gear 124.

The rotary joint 150 may include the rotary cover 151, a rotation axis groove 1512 formed on a circumference of the axis of rotation 1511 of the rotary cover 151, and the third bearing 153 disposed between a cylindrical end portion 1243 protruding from the base gear 124 and an inner wall of the rotation axis groove 1512. Axes of rotation 1513 of the at least one planetary gear 152 may be formed as an integral body on the rotary cover 151.

Figure 7:
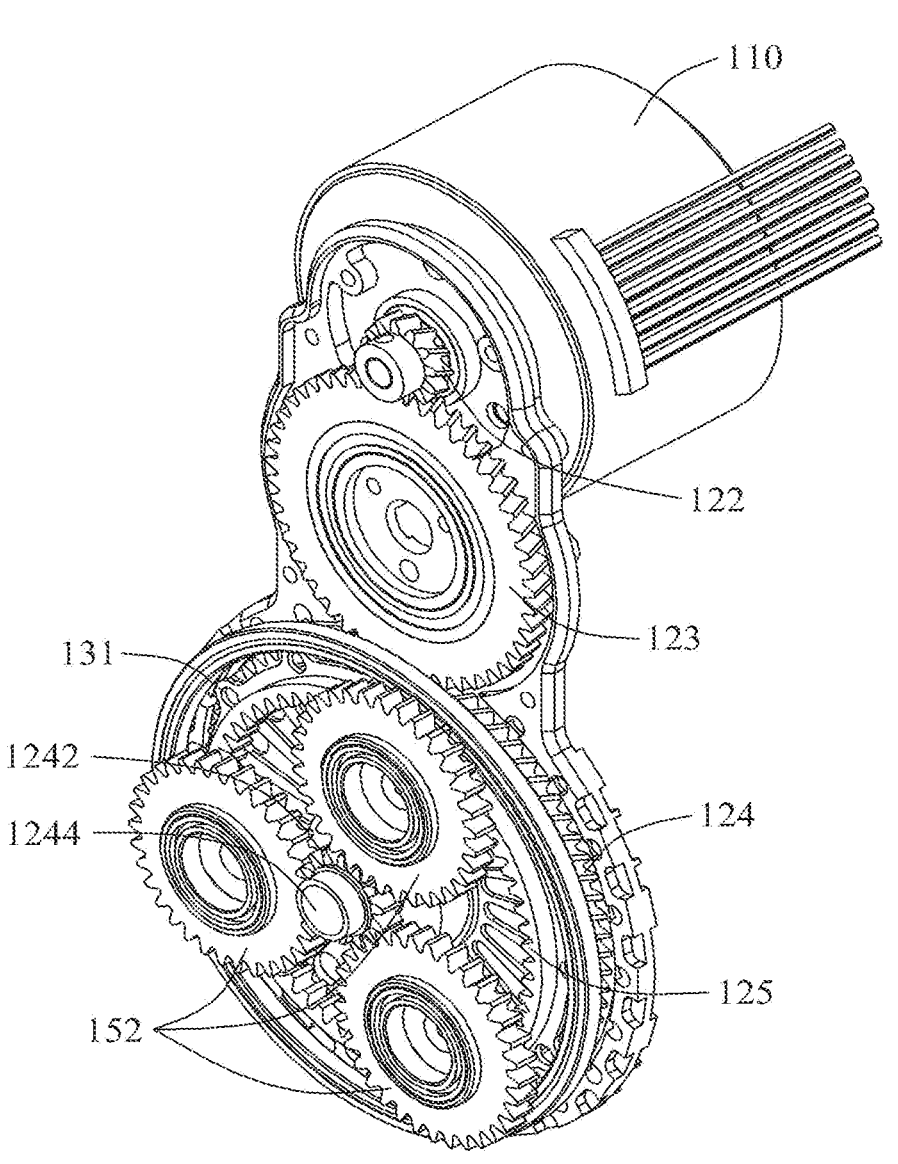
FIG. 7 is a partial exploded view of a driving module according to example embodiments.
Figure 8:
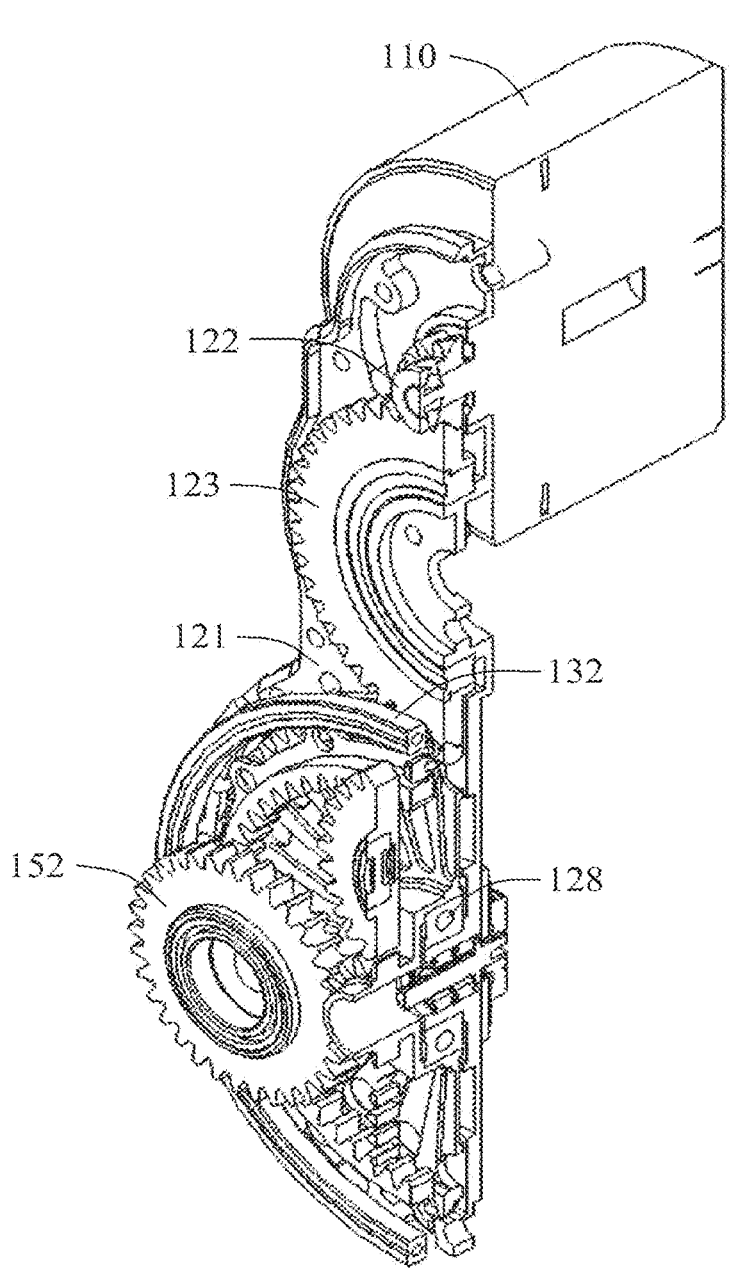
FIG. 8 is a cross-sectional perspective view of the driving module of FIG. 7.
Figure 9:
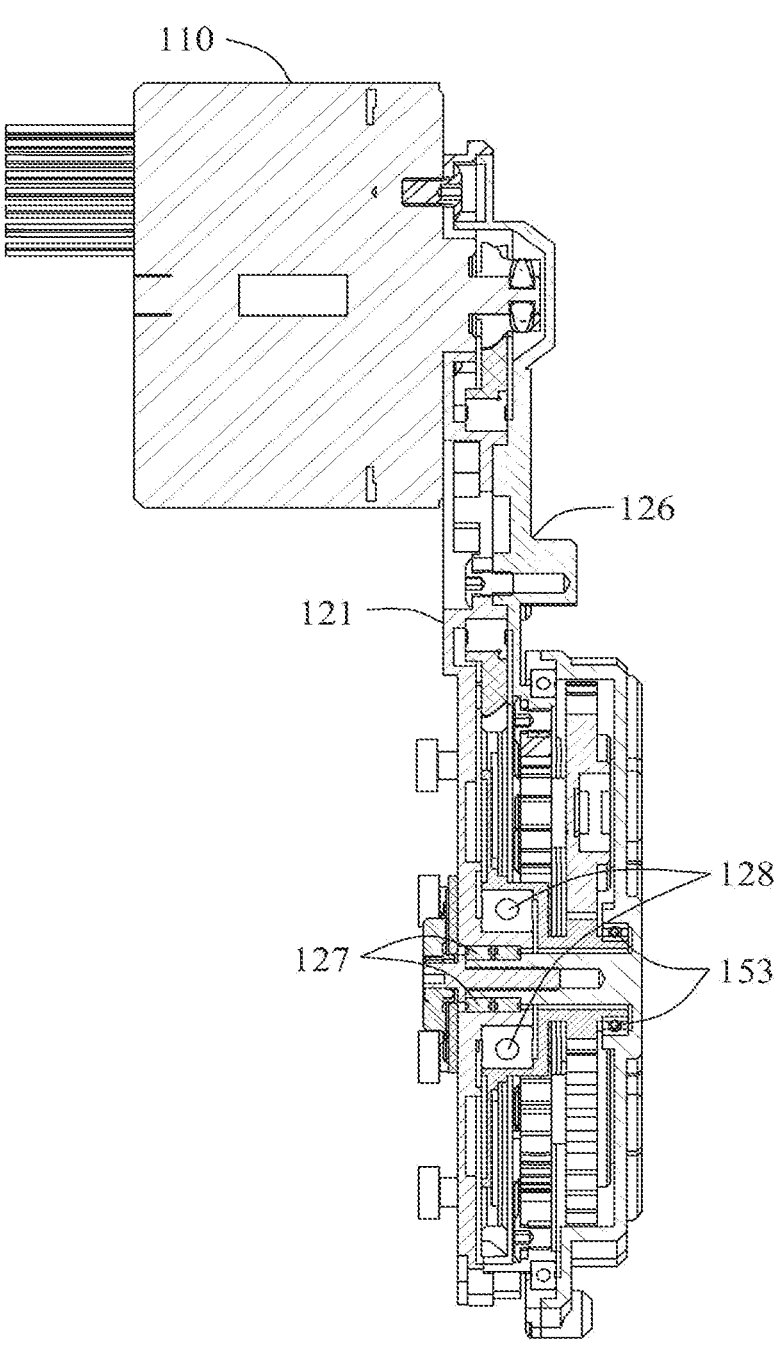
FIG. 9 is a cross-sectional view of a driving module according to example embodiments.
Figure 10:
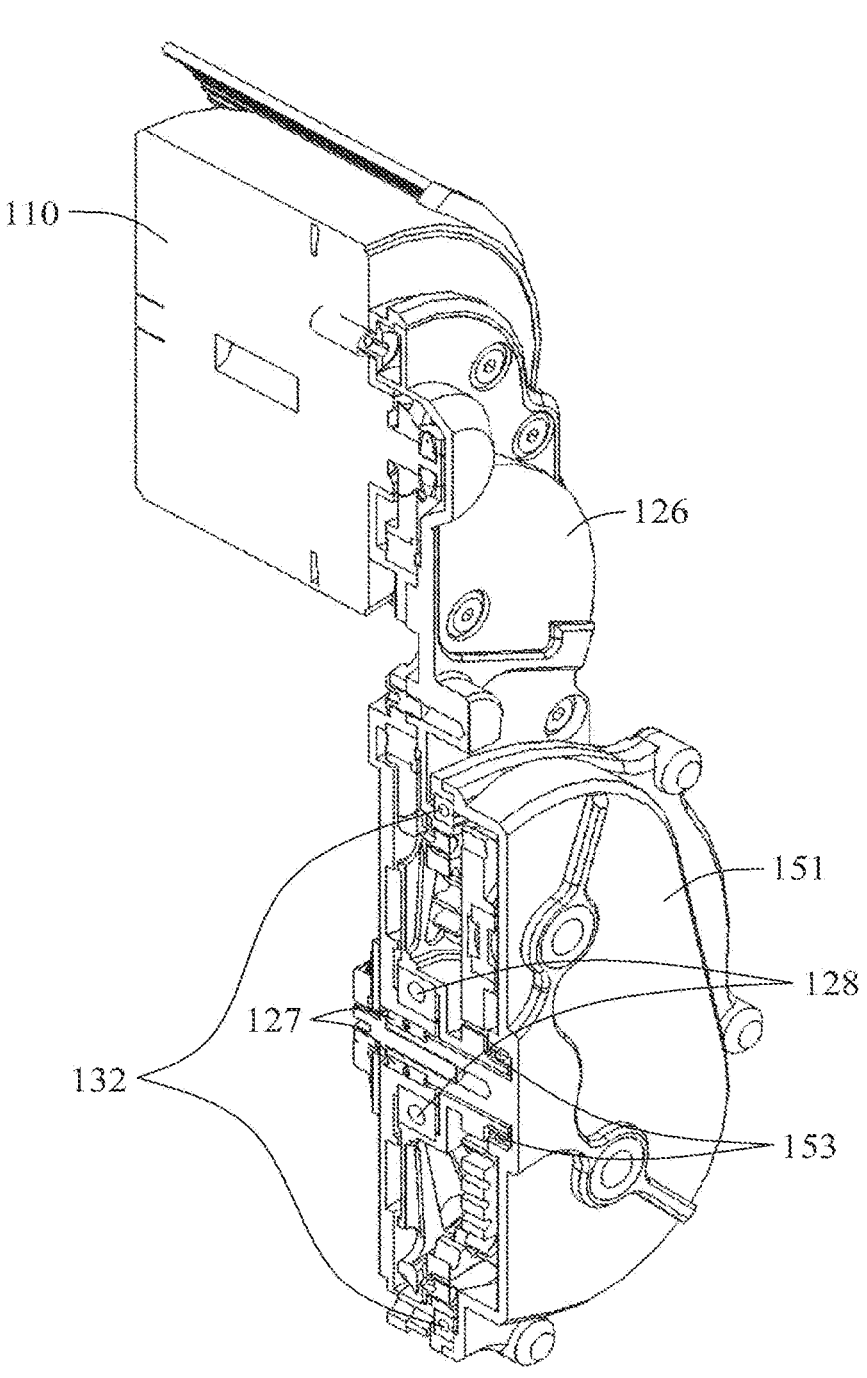
FIG. 10 is a cross-sectional perspective view of a driving module according to example embodiments.

FIG. 7 is a partial exploded view of the driving module 100 according to example embodiments, and FIG. 8 is a cross-sectional perspective view of the driving module 100 of FIG. 7. FIG. 9 is a cross-sectional view of the driving module 100 according to example embodiments, and FIG. 10 is a cross-sectional perspective view of the driving module 100 according to example embodiments.

Referring to FIGS. 7 through 10, the first frame 121 may include the receiving protrusion 129 including the groove 130 configured to receive the axis of rotation 1511 of the rotary joint 150. The first bearing 127 may be provided between an inner wall of the groove 130 and an outer wall of the axis of rotation 1511 of the rotary joint 150.

The second bearing 128 may be provided between the base gear 124 and the first frame 121 to assist a rotation of the base gear 124.

The rotation axis groove 1512 may be formed on a circumference of the axis of rotation 1511 of the rotary cover 151, and the third bearing 153 may be provided between an outer wall of the cylindrical end portion 1243 protruding from the base gear 124 and an inner wall of the rotation axis groove 1512.

The rotary joint 150 including the rotary cover 151 provided in a form of a shaft-integrated frame may be supported by the joint bearing 132. A thin section bearing having an extremely large diameter may be used for the joint bearing 132. In this example, a stiffness with respect to a torsion of the rotary cover 151 may increase.

Both ends of the base gear 124 disposed at a center of the gear train 120 may be supported by the rotary cover 151 and the first frame 121. In detail, one end of the base gear 124 may be supported by the third bearing 153 and an axis of rotation of the rotary cover 151 in a form of a shaft-integrated frame constituting the rotary joint 150. The other end of the base gear 124 may be supported by the first bearing 127 and the first frame 121 in a form of a shaft-integrated frame of the gear train 120.

Figure 11:
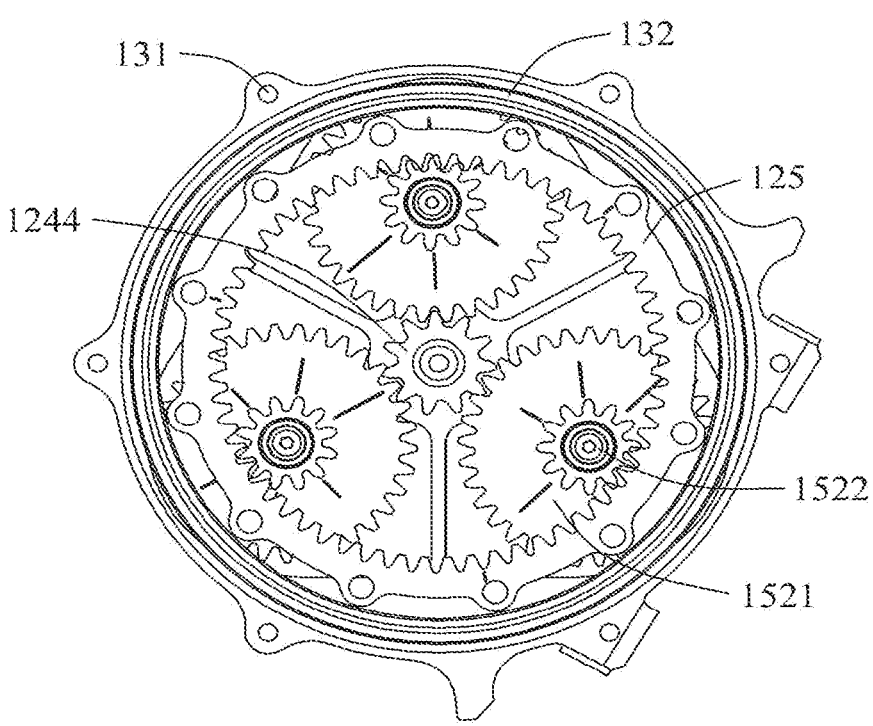
FIG. 11 is a view illustrating an operation of a planetary gear according to example embodiments.

FIG. 11 is a view illustrating an operation of the planetary gear 152 according to example embodiments.

Structures of the base gear 124, the ring gear 125, and the planetary gear 152 will be described in detail with reference to FIG. 11.

The planetary gear 152 may include a large-diameter gear 1521 and a small-diameter gear 1522, and the large-diameter gear 1521 may be engaged with the small-diameter gear 1244 of the base gear 124. The small-diameter gear 1522 may be engaged with the ring gear 125.

By a torque generated by the driving source 110, the small-diameter gear 1244 of the base gear 124 may be engaged with the small-diameter gear 1522 of the planetary gear 152 to generate a rotation, and the ring gear 125 may be engaged with the large-diameter gear 1521 of the planetary gear 152 to restrict a rotation.

Thus, the plurality of planetary gears 152 may revolve along a circumference formed by the plurality of planetary gears 152. Since the axes of rotation of the planetary gears 152 may be integrated on the rotary cover 151, the rotary cover 151 may rotate on a center of the circumference formed by the plurality of planetary gears 152.

Figure 12A:
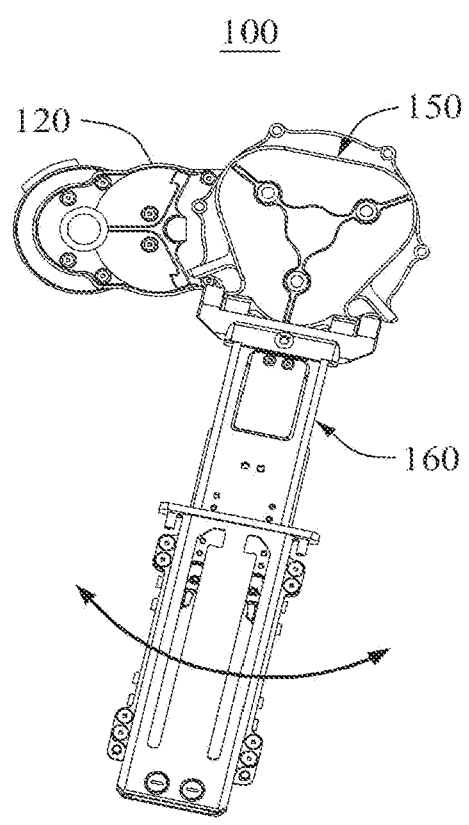
FIGS. 12A and 12B are views illustrating an operation of a rotary joint according to example embodiments.
Figure 12B:
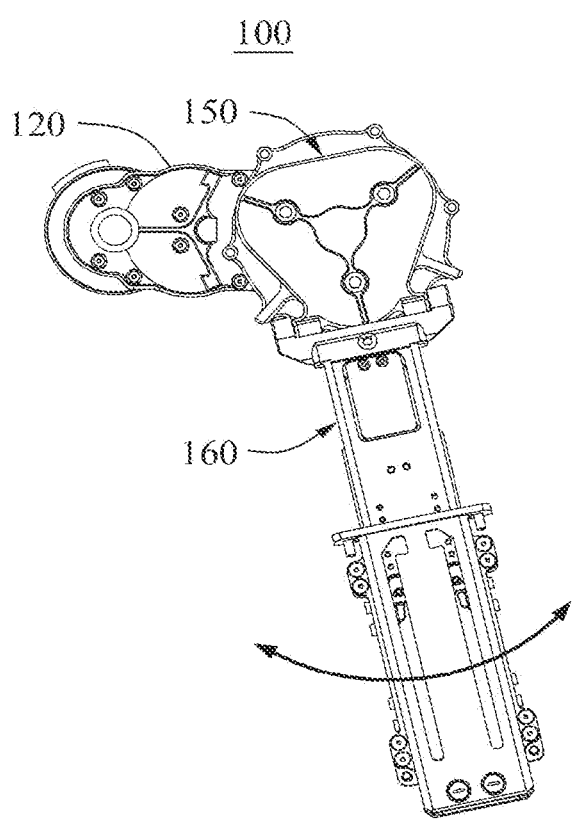

FIGS. 12A and 12B are views illustrating an operation of the rotary joint 150 according to example embodiments.

Referring to FIGS. 12A and 12B, the driving source 110 may be attached to the gear train 120, and the rotary joint 150 may relatively rotate with respect to the gear train 120 using driving power. Based on a rotation direction of the rotary joint 150, the connecting member 160 connected to the rotary joint 150 may rotate in a forward or backward direction.

In the modularized structure, the driving source 110 may be detachable from the gear train 120, and the gear train 120 may be detachable from the rotary joint 150.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A motion assistance apparatus comprising:
a fixing member configured to attach to a first portion of a body of a user;
a driver including,
a driving source on one side of the fixing member,
a gear train including an input gear, an idle gear and a base gear, the input gear configured to be connected to the driving source, the idle gear configured to be engaged with the input gear, the base gear configured to engaged with the idle gear, and
a rotary joint connected to the base gear; and
a support configured to support a second portion of the body of the user, and to move in response to a driving power,
wherein the input gear, the idle gear and the base gear are arranged side by side in a direction across an axis of rotation of the input gear,
wherein the gear train further comprises a first frame and a second frame configured to cover the input gear, the idle gear and the base gear,
wherein the first frame comprises a rotational shaft of the idle gear.

2. The motion assistance apparatus of claim 1, the rotary joint including at least one planetary gear connected to the base gear, wherein the at least one planetary gear is configured to rotate about an axis of rotation of the at least one planetary gear, the axis of rotation of the at least one planetary gear being an integral body on an inner side of the rotary joint.

3. The motion assistance apparatus of claim 1, wherein the driving source is configured to attach to the gear train, and the rotary joint is configured to relatively rotate with respect to the gear train using the driving power.

4. The motion assistance apparatus of claim 1, wherein the driving source is configured to detach from the gear train, and the gear train is configured to detach from the rotary joint.

* * * * *